(12) United States Patent
Verbeek et al.

(10) Patent No.: US 7,015,333 B2
(45) Date of Patent: Mar. 21, 2006

(54) PROCESS FOR PREPARATION OF IMIDAZOLYL COMPOUNDS

(75) Inventors: Jan-Maarten Verbeek, Weesp (NL); Paulus F. C. Van Der Meij, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 265 days.

(21) Appl. No.: 10/712,258

(22) Filed: Nov. 14, 2003

(65) Prior Publication Data

US 2004/0158077 A1    Aug. 12, 2004

(30) Foreign Application Priority Data

Nov. 18, 2002   (EP) .................................. 02079838
Nov. 18, 2002   (NL) .................................. 1021939

(51) Int. Cl.
  *C07D 403/06*   (2006.01)
(52) U.S. Cl. .................................... 548/311.4; 548/336
(58) Field of Classification Search ............. 548/311.4, 548/336
See application file for complete search history.

(56) References Cited

U.S. PATENT DOCUMENTS

| | | | | |
|---|---|---|---|---|
| 4,695,578 A | * | 9/1987 | Coates et al. ................ | 514/397 |
| 4,939,136 A | * | 7/1990 | Haeck et al. ................ | 514/183 |
| 5,438,068 A | * | 8/1995 | Eeckhout et al. ........... | 514/397 |
| 5,663,343 A | * | 9/1997 | van der Meij et al. ....... | 546/72 |

FOREIGN PATENT DOCUMENTS

EP         0297851 B      1/1989

OTHER PUBLICATIONS

Chemical Abstract No. XP002239462, Ahtaki, H. "Synthetic routes to benz- and aphthindenoquinolines" Journal of the Chemical Scoiety, 17 (1967) pp. 1581-1582.
Chemical Abstract No. XP002239463, Korepin, A. et al. "N-Substituted tetrahydro-1,3-oxazines and oxazolidines 1. A new version fo the Mannich-reaction involving amino alcohols" 50(1) (2001) pp. 104-109.
International Search Report.

\* cited by examiner

*Primary Examiner*—Kamal A. Saeed

(74) *Attorney, Agent, or Firm*—Crowell & Moring LLP

(57) ABSTRACT

A method for preparing an imidazolyl compound corresponding to the formula (I)

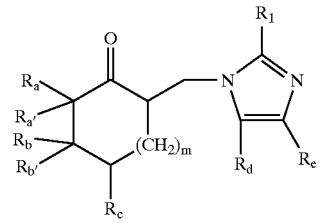

by reacting a compound corresponding to formula (II)

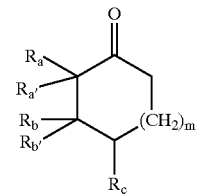

with a compound corresponding to formula (III)

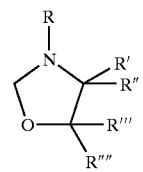

and then reacting the product with a compound corresponding to formula (IV)

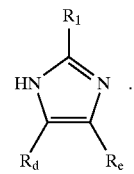

10 Claims, No Drawings

PROCESS FOR PREPARATION OF IMIDAZOLYL COMPOUNDS

BACKGROUND OF THE INVENTION

The present invention relates to a process for the preparation of imidazolyl compounds.

1,2,3,9-Tetrahydro-9-methyl-3-[2-methyl-1H-imidazol-1-yl)methyl]-4H-carbazol-4-one (ondansetron) is known from EP191562 and U.S. Pat. No. 4,695,578. These patent publications describe a general class of compounds including ondansetron and homologous compounds, their preparation and their uses as potent selective antagonists at "neuronal" 5-hydroxytryptamine receptors and in the treatment of migraine and psychotic disorders.

(10R)-5,6,9,10-Tetrahydro-10-[(2-methyl-1H-imidazol-1-yl)methyl]-4H-pyrido[3,2,1-jk]-carbazol-11(8H)-one (cilansetron) (also known as (R)-(−)-4,5,6,8,9,10-hexahydro-10-[(2-methyl-1H-imidazol-1-yl)methyl]-11H-pyrido-[3,2,1-jk]-carbazol-11-one) is known from U.S. Pat. No. 4,939,136 (=EP 297,651), from U.S. Pat. No. 5,438,068 (=EP 601,345) and from U.S. Pat. No. 5,663,343 (=EP 768,309). The first patent describes a general class of compounds, including cilansetron and homologous compounds, their preparation and their use as 5-HT antagonists. The second patent describes the use of selected compounds of this type for the treatment of certain diseases, and the third patent describes the preparation of enantiomerically pure compounds and their hydrochloride monohydrate.

It is a common feature of the above compounds that they contain a substituted imidazolyl group attached via a methylene bridge to the α-position relative to the keto group of the carbazole system. Several possibilities for the synthesis of these compounds are described in the aforementioned patent publications. A common feature in these syntheses is that the substituted imidazolyl group is introduced by means of a Mannich reaction, followed by a deamination to yield an intermediate exomethylene compound which is reacted with the substituted imidazolyl group (see scheme 1 for an example).

A drawback of this synthesis route is that the yield in this sequence of reaction steps is rather low. In U.S. Pat. No. 4,695,578 the first step, which is normally gives the lowest yield, is not described, and the second step (Example 7 of U.S. Pat. No. 4,695,578) gives a yield of 68%. In U.S. Pat. No. 4,939,136 the first step (Example 1c of U.S. Pat. No. 4,939,136) has a yield of 53% and the second step (Example 1d of U.S. Pat. No. 4,939,136) a yield of 87%. During scale-up it appeared that this route gives rise to the formation of a considerable amount of tar-like by-products.

SUMMARY OF THE INVENTION

It is an object of the present invention to provide an alternative process for preparing imidazolyl-compounds.

Another object of the process is to provide a process for preparing imidazolyl-compounds which is highly cost effective.

A further object of the invention is to provide a process for preparing imidazolyl-compounds which produces relatively high yields of the desired product.

It is also an object of the invention to provide a process for preparing imidazolyl-compounds with short reaction times compared with prior art processes.

An additional object of the invention is to provide a process for preparing imidazolyl-compounds which exhibits fewer side reactions.

Yet another object of the invention is to provide a process for preparing imidazolyl-compounds which yields final product of higher quality.

A still further object of the invention is to provide a process for preparing imidazolyl-compounds which uses non-diluted reaction conditions and an environmentally acceptable solvent.

These and other objects are achieved in accordance with the present invention by providing a process for preparing an imidazolyl compound as described and claimed hereinafter.

It has surprisingly been found that this type of imidazolyl compound can easily be prepared using a substituted oxazolidine compound for the introduction of the methylene bridge. Thus, the present invention relates to a method for preparation of an imidazolyl compound corresponding to the formula (I)

Scheme 1

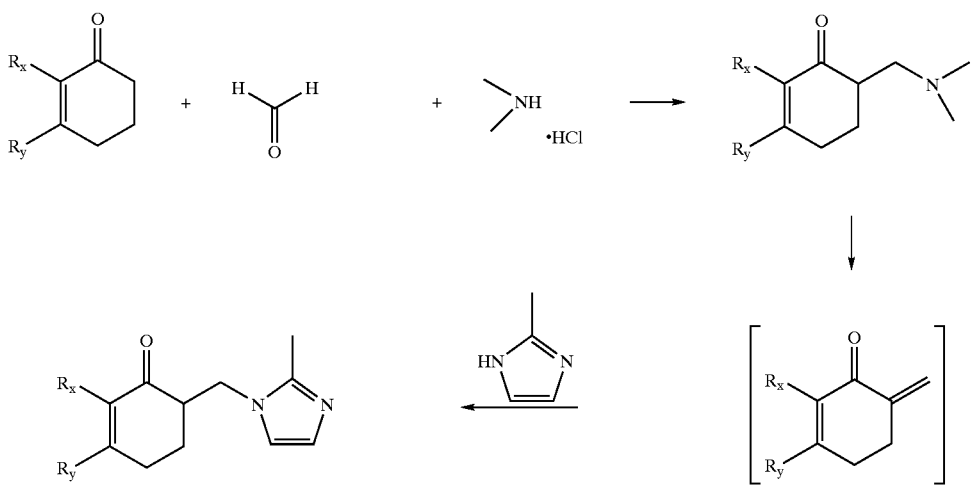

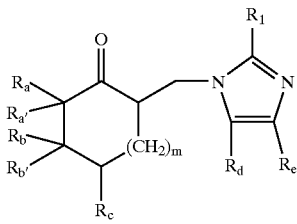

wherein:

$R_a$ and $R_b$ are each individually selected from the group consisting of $(C_1-C_6)$alkyl, $(C_1-C_6)$ alkoxyalkyl, and optionally substituted aryl and heteroaryl; or $R_a$ and $R_b$ together form a further homocyclic or heterocyclic system comprising one or more rings;

$R_{a'}$ and $R_{b'}$ are each hydrogen or together form a carbon-carbon double bond, said carbon-carbon double bond optionally being part of an aromatic system;

$R_c$ is hydrogen, $(C_1-C_6)$alkyl, $(C_1-C_6)$alkoxy, $(C_1-C_6)$ alkoxyalkyl or halogen;

$R_d$ is hydrogen or $(C_1-C_4)$alkyl;

$R_e$ is hydrogen or $(C_1-C_4)$alkyl;

m is 1 or 2; and $R_1$ is hydrogen or $(C_1-C_4)$alkyl; or an acid addition salt thereof; said method comprising a) reacting a compound corresponding to the formula (II)

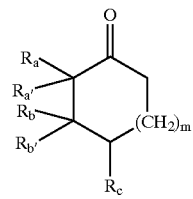

wherein $R_a$, $R_{a'}$, $R_b$ and $R_{b'}$ have the meanings defined above; with a compound of the formula (III)

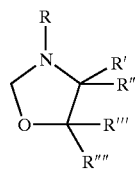

wherein:

R is a hydrogen, a $(C_1-C_4)$alkyl group optionally substituted with a hydroxygroup, or an optionally substituted aryl group, and R', R", R'" and R"" are each individually a hydrogen or a $(C_1-C_4)$alkyl group; and then b) reacting a product of step a) with a compound corresponding to the formula (IV)

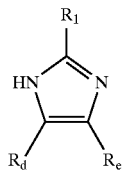

wherein $R_1$, $R_d$ and $R_e$ have the meanings defined above; and c) optionally reacting a product of step b) with an acid to obtain an acid addition salt.

Alkyl groups of the present invention include straight-chained, branched and cyclic alkyl radicals containing up to 6 carbon atoms. Suitable alkyl groups may be saturated or unsaturated. Further, an alkyl group may also be substituted one or more times with substituents selected from the group consisting of aryl, halo, hydroxy, cyano, monoalkyl amino and dialkyl amino.

Aryl groups of the present invention include aryl radicals which may contain up to 6 hetero atoms. An aryl group may also be optionally substituted one or more times with a substituent selected from the group consisting of aryl, $(C_1-C_6)$alkyl, halo, hydroxy, cyano, monoalkyl amino and dialkyl amino, and it may also be fused with another aryl group or with one or more cycloalkyl rings. Suitable aryl groups include, e.g., phenyl, naphthyl, tolyl, imidazolyl, pyridyl, pyrroyl, thienyl, pyrimidyl, thiazolyl and furyl groups.

As used herein, the term "homocyclic system" means a system containing at least one saturated or unsaturated cyclic group containing only carbon atoms and hydrogen atoms. The term "heterocyclic system" as used herein means a system containing at least one saturated or unsaturated cyclic group which includes one or more heteroatoms such as N, O or S. Both the homocyclic and heterocyclic systems may optionally be substituted with one or more substituents selected from the group consisting of alkyl, aryl, cyano, halogen, hydroxyl, monoalkylamino and dialkylamino groups.

In one preferred embodiment of the invention $R_c$ is hydrogen or $(C_1-C_6)$alkyl, $R_d$ is hydrogen or $(C_1-C_4)$alkyl; $R_e$ is hydrogen or $(C_1-C_4)$alkyl; and $R_1$ is hydrogen, methyl or ethyl.

The reaction according to the invention is especially useful for the preparation of compounds corresponding to the formula (Ia)

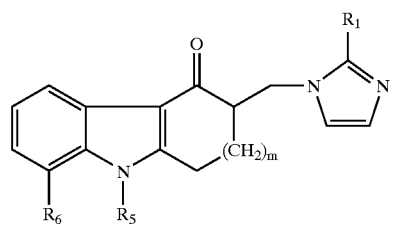

wherein:
m is 1 or 2;
$R_1$ is hydrogen, methyl or ethyl;
$R_5$ is a $(C_1-C_4)$ alkyl; and
$R_6$ is a hydrogen or a $(C_1-C_4)$alkyl, or R$_5$ and R$_6$ together with the intermediate atoms form a 5, 6, or 7 membered ring, optionally substituted with one or two substituents selected from the group consisting of halogen, hydroxy, (C$_1$–C$_4$)alkyl, (C$_1$–C$_4$)alkoxyalkyl and (C$_1$–C$_4$)alkoxy.

In this case the starting compound is a compound corresponding to the formula (IIa)

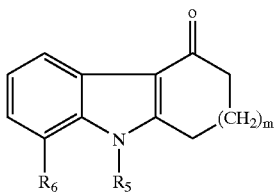

This compound is further referred to as a carbazolone compound.

Preferred compounds corresponding to formula Ia are the compound in which m=1 and R$_5$ and R$_6$ together with the intermediate atoms form a 6-membered ring and the compound in which m=1, R$_5$ is methyl and R$_6$ is hydrogen. For the first compound the yield for the process starting with 5,6,9,10-tetrahydro-4H-pyrido[3,2,1-jk]carbazol-11(8H)-one and 3-oxazolidineethanol is 77% (see Example 2) compared with the overall yield of 46% in the process according to U.S. Pat. No. 4,939,136 (Examples Ic and Id). Higher yields may be obtained at a production scale.

In the substituted oxazolidine, preferably one of R' and R" and one of R'" and R"" is hydrogen, inasmuch as an oxazolidine which is disubstituted on the same carbon atom, such as 4,4-dimethyloxazolidine, gives a lower yield in the reaction. Preferred oxazolidines are 3-oxazolidineethanol and 3-ethyl-oxazolidine. The most preferred oxazolidine is 3-oxazolidineethanol.

The reaction is carried out in an acidic medium, and the degree of acidity required depends on the activation of the system that has to react. In the case of carbazolone systems, the medium should be highly acidic. Examples of suitable acids for use in such a case include methanesulfonic acid, trifluoromethanesulfonic acid, p-toluenesulfonic acid and gaseous HCl in an alcoholic medium.

In order to obtain a high yield, the reaction solution should contain only a low amount of water. The amount of water should preferably be below 0.6% (V/V), more preferably below 0.3% V/V, and most preferably below 0.1% V/V.

The optimal reaction temperature is dependent on the starting material and the solvent and differs for the two reaction steps. The first step of the reaction can be performed at temperatures between 40° C. and 110° C. For the carbazolone systems the preferred reaction temperature in the first step is between 50° C. and 90° C., and the most preferred temperature is about 70° C. The second step can generally be carried out at temperatures between 100° C. and 140° C. For the carbazolone systems the preferred reaction temperature in the second step is between 110° C. and 130° C., and the most preferred temperature is about 120° C.

The reaction can be performed in different solvents such as dipolar aprotic solvents like dimethylformamide (DMF) or in alcohols. Preferred solvents are C$_4$–C$_7$ alcohols. The choice of solvent may depend on the desired reaction temperature. Examples of suitable alcohols include 1-butanol, 1-hexanol and isoamyl alcohol. A preferred alcohol is 1-butanol. Also suitable are mixtures of aromatic hydrocarbons and alcohols, such as mixtures of toluene and an alcohol or mixtures of monochlorobenzene and an alcohol.

A preferred mixture is a mixture of monochlorobenzene and methanol. When a solvent mixture is used, the lower boiling solvent can be distilled off before the second step in order to attain higher reflux temperatures of the solvent system in the second step.

The ratio of the solvent volume to the amount of reactants in the mixture can be varied over a relatively broad range and depends on the solubility of the reactants. In general the ratio of the amount of solvent to the amount of reactants can typically range from about 1:1 to 15:1, where the ratio is expressed as the volume in ml of the solvent relative to the weight in grams of the reactants in the solvent. Preferably the ratio is about 1:1 to about 10:1. In the case of the carbazolone systems, the preferred ratio of the volume of solvent to the weight of reactants is about 4:1.

The products obtained can be crystallized from different solvents. Examples of solvents for the cyrstallisation of free bases include aromatic hydrocarbons such as toluene. The hydrochloric acid salts can be crystallized, e.g., from alcoholic solvents such as isopropanol or 1-butanol.

The following examples are only intended to further illustrate the invention in more detail, and therefore these examples are not deemed to restrict the scope of the invention in any way.

EXAMPLE 1

Materials and Methods 5,6,9,10-Tetrahydro-4H-pyrido[3,2,1-jk]carbazol-11 (8H)-one was produced as described in published European patent application no. EP 375,045. 3,4-Dihydro-1(2H)-naphthalenone was obtained from a commercial source. 1,2,3,9-Tetrahydro-9-methyl-4H-carbazol-4-one was produced as described in U.S. Pat., No. 3,892,766 from Warner-Lambert Company and Elz, S. and Heil, W., Bioorganic & Medicinal Chemistry Letters 1995, 5, 667–672. Methanesulfonic acid was obtained from a commercial source.

NMR spectra were measured on a Varian VXR 200 and MS spectra on a Finnigan TSQ 7000. HPLC analyses were performed on a HP1050 system with a Separations 757 detector (250 nm) and a Separations Marathon XT column oven at 35° C. The column used was a Zorbax XDB C8 colomn 15×0.3 cm. The eluent was prepared as follows: mix 2 liters water, 2 ml triethylamine and 5 ml 25% ammonia, buffer the resulting mixture at pH=4 with formic acid, and add 0.5 liter of acetonitrile. The flow was 1 ml/min.

EXAMPLE 1a

Preparation of Oxazolidines

3-Oxazolidineethanol was prepared as follows:

Equimolar amounts of diethanolamine and paraformaldehyde in 1-butanol were heated to 70° C. After 1 hour reaction time the resulting water was removed by azeotropic distillation with 1-butanol.

3-Ethyl-oxazolidine was prepared according to Heany, H. et al., Tetrahedron 1997, 53, 14381–96.

4,4-Dimethyl-oxazolidine is commercially available and was purchased as a 75% w/w solution in water. The 4,4-dimethyl-oxazolidine was extracted from the water layer by washing with dichloromethane/saturated NaCl-solution. The dichloromethane layer was dried over anhydrous sodium sulfate and subsequently evaporated.

EXAMPLE 2

Reaction of 5,6,9,10-tetrahydro-4H-pyrido[3,2,1-jk] carbazol-11(8H)-one with 3-oxazolidineethanol 5,6,9,10-Tetrahydro-4H-pyrido[3,2,1-jk]carbazol-11 (8H)-one (25.00 g≡111.0 mmole) and methanesulfonic acid (17.06 g≡177.5 mmole) in 1-butanol (100 ml) were heated to 70° C. In 3 minutes a solution of 3-oxazolidineethanol (19.49 g≡166.4 mmole) in 1-butanol (39 ml) was added. After 50 minutes at 80° C. 2-methylimidazole (45.55 g≡554.8 mmole) and 1-butanol (10 ml) were added. After 1.5 hours at 120° C. the reaction mixture was partly evaporated till 30 ml of 1-butanol remained.

At 70° C., 75 ml of toluene and 50 ml of water were added to the residue. The layers were separated. The water layer was extracted with 75 ml of toluene. The combined toluene layers were washed three times with 100 ml of water.

The organic layer was evaporated to dryness, and subsequently 125 ml of 1-butanol was added. To the resulting solution 12.5 ml of 36% m/m hydrochloric acid was added. After stirring for 2 hours at room temperature, the resulting solid was filtered out and washed with 1-butanol and MTBE. Yield after drying: 30.40 g (77.0%) 5,6,9,10-tetrahydro-10-[(2-methyl-1H-imidazol-1-yl)methyl]-4H-pyrido[3,2,1-jk]carbazol-11(8H)-one hydrochloride (77.0%). HPLC: ≧95%. $^1$H NMR [200 MHz, DMSO-d$^6$:CDCl$_3$ 4:1] δ 1.97(1H,m), 2.18 (3H,m), 2.68(3H,s), 2.95(2H,t), 3.00(1H,dd), 3.12(2H,m), 4.13(2H,m), 4.29(1H,dd), 4.66(1H,dd), 6.97(1H,d), 7.09 (1H,t), 7.55(1H,d), 7.68(1H,d) and 7.71(1H,d). MS [ESI] MH$^+$=320.

EXAMPLE 3

Reaction of 5,6,9,10-tetrahydro-4H-pyrido[3,2,1-jk] carbazol-11(8H)-one with 4,4-dimethyl-oxazolidine 5,6,9,10-Tetrahydro-4H-pyrido[3,2,1-jk]carbazol-11 (8H)-one (20.00 g≡88.8 mmole) and methanesulfonic acid (13.65 g≡142.0 mmole) in 1-butanol (60 ml) were heated to 70° C. In 2 minutes 4,4-dimethyl-oxazolidine (13.47 g≡133.2 mmole) in 1-butanol (10 ml) was added.

After 50 minutes at 80° C. 2-methylimidazole (36.45 g≡444.0 mmole) and butanol (10 ml) were added. After 2 hours at 120° C. the reaction mixture was partly evaporated till 20 ml of 1-butanol remained.

At 70° C., 60 ml of toluene and 40 ml of water were added to the residue. The layers were separated. The water layer was extracted with 60 ml of toluene. The combined toluene layers were washed three times with 80 ml of water.

The organic layer was evaporated to dryness, and subsequently 100 ml of 1-butanol was added. To the resulting solution 10.0 ml of 36% m/m hydrochloric acid was added. After stirring for 2 hours at room temperature the resulting solid was filtered out and washed with 1-butanol and MTBE. Yield after drying: 12.38 g 5,6,9,10-tetrahydro-10-[(2-methyl-1H-imidazol-1-yl)methyl]-4H-pyrido[3,2,1-jk]carbazol-11(8H)-one hydrochloride (39.2%). HPLC: ≧95%. $^1$H NMR and MS: see Example 2. The mother liquor contained 3.45 g (10.9%) of product.

EXAMPLE 4

Reaction of 5,6,9,10-tetrahydro-4H-pyrido[3,2,1-jk] carbazol-11(8H)-one with 3-ethyl-oxazolidine 5,6,9,10-Tetrahydro-4H-pyrido[3,2,1-jk]carbazol-11 (8H)-one (20.00 g≡88.8 mmole) and methanesulfonic acid (13.65 g≡142.0 mmole) in 1-butanol (60 ml) were heated to 70° C. In 2 minutes 3-ethyl-oxazolidine (13.46 g≡133.2 mmole) in 1-butanol (10 ml) was added.

After 50 minutes at 80° C. 2-methylimidazole (36.45 g≡444.0 mmole) and 1-butanol (10 ml) were added. After 2 hours at 120° C. the reaction mixture was partly evaporated till 20 ml of 1-butanol remained.

At 70° C., 60 ml of toluene and 40 ml of water were added to the residue. The layers were separated. The water layer was extracted with 60 ml of toluene. The combined toluene layers were washed three times with 80 ml of water.

The organic layer was evaporated to dryness, and subsequently 100 ml of 1-butanol was added. To the resulting solution 10.0 ml of 36% m/m hydrochloric acid was added. After stirring for 2 hours at room temperature the resulting solid was filtered out and washed with 1-butanol and MTBE. Yield after drying: 22.10 g (70.0%) 5,6,9,10-tetrahydro-10-[(2-methyl-1H-imidazol-1-yl)methyl]-4H-pyrido[3,2,1-jk]carbazol-11(8H)-one hydrochloride (70.0%). HPLC: ≧95%. $^1$H NMR and MS: see Example 2.

EXAMPLE 5

Reaction of 3,4-dihydro-1(2H)-naphthalenone with 3-oxazolidineethanol 3,4-Dihydro-1(2H)-naphthalenone (12.98 g≡88.8 mmole) and methanesulfonic acid (13.65 g≡142.0 mmole) in 1-butanol (60 ml) were heated to 50° C. In 2 minutes a solution was added of 3-oxazolidineethanol (15.59 g≡133.1 mmole) in 1-butanol (14 ml).

After 50 minutes at 80° C. 2-methylimidazole (36.45 g≡444.0 mmole) and 1-butanol (10 ml) were added. After 2 hours at 120° C. the reaction mixture was partly evaporated till 20 ml of 1-butanol remained.

At 70° C., 60 ml of toluene and 40 ml of water were added to the residue. The layers were separated. The water layer was extracted with 60 ml of toluene. The combined toluene layers were washed three times with 80 ml of water.

The organic layer was evaporated to dryness and subsequently 100 ml of 1-butanol was added. To the resulting solution 10.0 ml of 36% m/m hydrochloric acid was added. The resulting solution was evaporated until an end volume of 60 ml was reached. After stirring for 2 hours at room temperature the resulting solid was filtered out and washed with 1-butanol and MTBE. Yield after drying: 15.28 g (62.2%) 3,4-dihydro-2-[(2-methyl-1H-imidazol-1-yl)methyl]-1(2H)-naphthalenone hydrochloride. HPLC: ≧95%. $^1$H NMR[200 MHz, DMSO-d$^6$:CDCl$_3$ 4:1] δ 2.00 (2H,m), 2.73 (3H,s), 3.20 (3H,m), 4.27 (1H,dd), 4.68 (1H,dd), 7.35 (2H,t), 7.55 (2H,m), 7.70 (1H,d) and 7.90 (1H,d). MS [ESI] MH$^+$=241. The mother liquor contained 3.28 g (13.3%) of product.

EXAMPLE 6

Reaction of 3,4-dihydro-1(2H)-naphthalenone with 4,4-dimethyl-oxazolidine 3,4-Dihydro-1(2H)-naphthalenone (12.98 g≡88.8 mmole) and methanesulfonic acid (13.65 g≡142.0 mmole) in 1-butanol (60 ml) were heated to 70° C. In 2 minutes 4,4-dimethyl-oxazolidine (13.46 g≡133.1 mmole) in 1-butanol (10 ml) was added. After 50 minutes at 80° C. 2-methylimidazole (36.45 g≡444.0 mmole) and 1-butanol (10 ml) were added. After 2 hours at 120° C. the reaction mixture was partly evaporated till 20 ml of 1-butanol remained.

At 70° C., 60 ml of toluene and 40 ml of water were added to the residue. The layers were separated. The water layer was extracted with 60 ml of toluene. The combined toluene layers were washed three times with 80 ml of water.

The organic layer was evaporated to dryness, and subsequently 100 ml of 1-butanol was added. To the resulting solution 10.0 ml of 36% m/m hydrochloric acid was added. The resulting solution was evaporated until an end volume of 50 ml was reached. After stirring for 2 hours at 0° C., the resulting solid was filtered out and washed with 1-butanol and MTBE. Yield after drying: 14.13 g (57.5%) 3,4-dihydro-2-[(2-methyl-1H-imidazol-1-yl)methyl]-1(2H)-naphthalenone hydrochloride. HPLC: ≧95%. $^1$H NMR and MS: see Example 5. The mother liquor contained 2.33 g (9.5%) of product.

EXAMPLE 7

Reaction of 3,4-dihydro-1(2H)-naphthalenone with 3-ethyl-oxazolidine 3,4-Dihydro-1(2H)-naphthalenone (12.98 g≡88.8 mmole) and methanesulfonic acid (13.65 g≡142.0 mmole) in 1-butanol (60 ml) were heated to 50° C. In 2 minutes 3-ethyl-oxazolidine (13.46 g≡133.1 mmole) in 1-butanol (10 ml) was added. After 50 minutes at 80° C. 2-methylimidazole (36.45 g≡444.0 mmole) and 1-butanol (10 ml) were added. After 2 hours at 120° C. the reaction mixture was partly evaporated till 20 ml of 1-butanol remained.

At 70° C., 60 ml of toluene and 40 ml of water were added to the residue. The layers were separated. The water layer was extracted with 60 ml of toluene. The combined toluene layers were washed three times with 80 ml of water.

The organic layer was evaporated to dryness, and subsequently 100 ml of 1-butanol was added. To the resulting solution 10.0 ml of 36% m/m hydrochloric acid was added. The resulting solution was evaporated until an end volume of 50 ml was reached. After stirring for 2 hours at 0° C. the resulting solid was filtered out and washed with 1-butanol and MTBE. Yield after drying: 17.30 g 3,4-dihydro-2-[(2-methyl-1H-imidazol-1-yl)methyl]-1(2H)-naphthalenone hydrochloride (70.4%). HPLC: ≧95%. $^1$H NMR and MS: see Example 5.

EXAMPLE 8

Reaction of 1,2,3,9-tetrahydro-9-methyl-4H-carbazol-4-one with 3-oxazolidineethanol 1,2,3,9-Tetrahydro-9-methyl-4H-carbazol-4-one (13.26 g≡66.5 mmole) and methanesulfonic acid (10.23 g≡106.4 mmole) in 1-butanol (45 ml) were heated to 90° C. In 2 minutes 11.68 g (99.8 mmole) of 3-oxazolidineethanol in 1-butanol (11 ml) was added.

After 50 minutes at 80° C. 2-methylimidazole (27.32 g≡332.5 mmole) and 1-butanol (8 ml) were added. After 2 hours at 120° C. 180 ml of toluene and 120 ml of water were added at 80° C. The layers were separated. The water layer was extracted with 180 ml of toluene and 60 ml of 1-butanol. The combined organic layers were washed twice with 240 ml of water. The organic layer was evaporated to dryness. 150 ml of 1-butanol and 10 ml of 36% m/m hydrochloric acid were added to the residue. At 0° C. crystallization soon occurred. After 1 hour at 0° C. the resulting crystals were filtered out, washed with 1-butanol and MTBE and subsequently dried: 15.39 g (70.1%) of 1,2,3,9-Tetrahydro-9-methyl-3-[(2-methyl-1H-imidazol-1-yl)methyl]-4H-carbazol-4-one hydrochloride were isolated. HPLC: ≧95%. $^1$H NMR [200 MHz, DMSO-d$^6$:CDCl$_3$ 4:1] δ 2.00 (1H,m), 2.20 (1H,m), 3.69 (3H,s), 3.09 (3H,m), 3.75 (3H,s), 4.30 (1H,dd), 4.67 (1H,dd), 7.23 (2H,m), 7.53 (2H,m), 7.69 (1H,d), 8.01 (1H, d). MS [ESI] MH$^+$=294. The mother liquor contained 3.19 g (14.5%) of product.

EXAMPLE 9

Reaction of 1,2,3,9-tetrahydro-9-methyl-4H-carbazol-4-one with 4,4-dimethyl-oxazolidine 1,2,3,9-Tetrahydro-9-methyl-4H-carbazol-4-one (13.26 g≡66.5 mmole) and methane-sulfonic acid (10.23 g≡106.4 mmole) in 1-butanol (45 ml) were heated to 90° C. In 2 minutes 4,4-dimethyl-oxazolidine (10.09 g≡99.9 mmole) in 1-butanol (8 ml) was added.

After 50 minutes at 80° C. 2-methylimidazole (27.32 g≡332.5 mmole) and 1-butanol (8 ml) were added. After 2 hours at 120° C. 180 ml of toluene and 120 ml of water were added at 80° C. The layers were separated. The water layer was extracted with 180 ml of toluene and 60 ml of 1-butanol. The combined organic layers were washed twice with 240 ml of water. The organic layer was evaporated to dryness. 150 ml of 1-butanol and 10 ml of 36% m/m hydrochloric acid were added to the residue. At 0° C. crystallization soon occurred. After 1 hour at 0° C. the resulting crystals were filtered out, washed with 1-butanol and MTBE and subsequently dried. 10.02 g (45.7%) of 1,2,3,9-tetrahydro-9-methyl-3-[(2-methyl-1H-imidazol-1-yl)methyl]-4H-carbazol-4-one hydrochloride were obtained. The mother liquor contained 2.70 g (12.3%) of product. HPLC: ≧95%. NMR and MS: see Example 8.

EXAMPLE 10

Reaction of 1,2,3,9-tetrahydro-9-methyl-4H-carbazol-4-one with 3-ethyl-oxazolidine 1,2,3,9-Tetrahydro-9-methyl-4H-carbazol-4-one (13.26 g≡66.5 mmole) and methane-sulfonic acid (10.23 g≡106.4 mmole) in 1-butanol (45 ml) were heated to 90° C. In 2 minutes 3-ethyl-oxazolidine (10.09 g≡99.9 mmole) in 1-butanol (8 ml) was added.

After 50 minutes at 80° C. 2-methylimidazole (27.32 g≡332.5 mmole) and 1-butanol (8 ml) were added. After 2 hours at 120° C. 180 ml of toluene and 120 ml of water were added at 80° C. The layers were separated. The water layer was extracted with 180 ml of toluene and 60 ml of 1-butanol. The combined organic layers were washed twice with 240 ml of water. The organic layer was evaporated to dryness. 150 ml of 1-butanol and 10 ml of 36% m/m hydrochloric acid were added to the residue. At 0° C. crystallization soon occurred. After 1 hour at 0° C. the resulting crystals were filtered out, washed with 1-butanol and MTBE and subsequently dried. 15.67 g (71.4%) of 1,2,3,9-tetrahydro-9-methyl-3-[(2-methyl-1H-imidazol-1-yl)methyl]-4H-carbazol-4-one hydrochloride were isolated. HPLC: ≧95%. NMR and MS: see Example 8. The mother liquor contained 2.06 g (9.4%) of product.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A method for preparing an imidazolyl compound corresponding to formula (I)

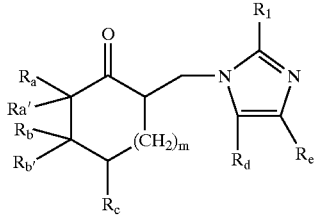

wherein:

$R_a$ and $R_b$ are each individually selected from the group consisting of $(C_1-C_6)$alkyl, $(C_1-C_6)$alkoxyalkyl, and optionally substituted aryl and heteroaryl; or $R_a$ and $R_b$ together form a further homocyclic or heterocyclic system comprising one or more rings;

$R_{a'}$ and $R_{b'}$ are each hydrogen or together form a carbon-carbon double bond, said carbon-carbon double bond optionally being part of an aromatic system;

$R_c$ is hydrogen, $(C_1-C_6)$alkyl, $(C_1-C_6)$alkoxy, $(C_1-C_6)$alkoxyalkyl or halogen;

$R_d$ is hydrogen or $(C_1-C_4)$alkyl;

$R_e$ is hydrogen or $(C_1-C_4)$alkyl;

m is 1 or 2; and $R_1$ is hydrogen or $(C_1-C_4)$alkyl; or an acid addition salt thereof; said method comprising:

a) reacting a compound corresponding to formula (II)

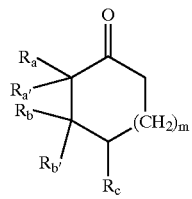

wherein $R_a$, $R_{a'}$, $R_b$ and $R_{b'}$ have the meanings defined above; with a compound corresponding to formula (III)

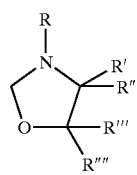

wherein:

R is a hydrogen, a $(C_1-C_4)$alkyl optionally substituted with a hydroxyl group, or an optionally substituted aryl group, and R', R", R''' and R'''' are each individually a hydrogen or a $(C_1-C_4)$alkyl group; and then b) reacting a product of step a) with a compound corresponding to formula (IV)

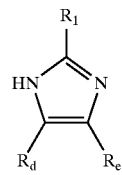

wherein $R_1$, $R_d$ and $R_e$ have the meanings defined above; and c) optionally reacting a product of step b) with an acid to obtain an acid addition salt.

2. A method according to claim 1, wherein $R_c$ is hydrogen or $(C_1-C_6)$alkyl, and $R_1$ is hydrogen, methyl or ethyl.

3. A method according to claim 1, for preparing an imidazolyl compound corresponding to the formula (Ia)

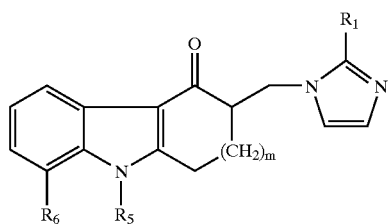

wherein:

m is 1 or 2;

$R_1$ is hydrogen, methyl or ethyl;

$R_5$ is $(C_1-C_4)$alkyl, and $R_6$ is hydrogen or $(C_1-C_4)$alkyl, or $R_5$ and $R_6$ together with the intermediate atoms form a 5, 6, or 7 member ring, optionally substituted with one or two substituents selected from the group consisting of halogen, hydroxyl, $(C_1-C_4)$alkyl, $(C_1-C_4)$alkoxyalkyl and $(C_1-C_4)$alkoxy; or a pharmaceutically acceptable acid addition salt thereof; said method comprising:

a) reacting a compound corresponding to the formula (IIa)

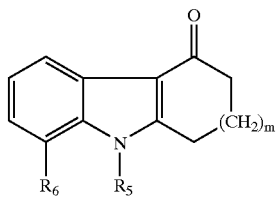

wherein $R_5$, $R_6$ and m have the meanings defined above; with a compound corresponding to the formula (III)

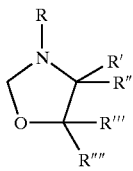

and then b) reacting a product of a) with a compound corresponding to the formula (IVa)

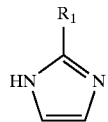

wherein R1 has the meaning given above.

4. A method according to claim 1, wherein R is a 2-hydroxyethyl group, and R', R", R''' and R'''' are each hydrogen.

5. A method according to claim 1, wherein m=1, and $R_5$ and $R_6$ together with the intermediate atoms form a 6-member ring.

6. A method according to claim 1, wherein m=1; $R_5$ is methyl, and $R_6$ is hydrogen.

7. A method according to claim 1, wherein the reaction is carried out in an alcoholic solvent.

8. A method according to claim 7, wherein the alcoholic solvent is 1-butanol.

9. A method according to claim 1, wherein the reaction is carried out in a mixture of an alcoholic solvent and an aromatic hydrocarbon.

10. A method according to claim 9, wherein said mixture is a mixture of methanol and chlorobenzene.

* * * * *